United States Patent [19]
Rasmussen

[11] Patent Number: 5,977,158
[45] Date of Patent: Nov. 2, 1999

[54] PHARMACEUTICAL FORMULATIONS COMPRISING LEVORMELOXIFENE COMPOUNDS

[75] Inventor: Stella Rudkær Rasmussen, Copenhagen, Denmark

[73] Assignee: Novo Nordisk A/S, Bagsvaerd, Denmark

[21] Appl. No.: 08/976,704

[22] Filed: Nov. 24, 1997

Related U.S. Application Data

[60] Provisional application No. 60/039,351, Mar. 18, 1997.

[30] Foreign Application Priority Data

Nov. 28, 1996 [DK] Denmark ................................ 1359/96
Nov. 7, 1997 [DK] Denmark ................................ 1265/97

[51] Int. Cl.$^6$ .................................................. A61K 31/40
[52] U.S. Cl. ............................................................. 514/422
[58] Field of Search .............................................. 514/422

[56] References Cited

U.S. PATENT DOCUMENTS

| | | | |
|---|---|---|---|
| 4,447,622 | 5/1984 | Salman et al. | 548/525 |
| 5,280,040 | 1/1994 | Labroo et al. | 514/422 |
| 5,407,955 | 4/1995 | Bryant et al. | 514/408 |
| 5,464,862 | 11/1995 | Labroo et al. | 514/422 |
| 5,472,977 | 12/1995 | Bryant et al. | 514/422 |
| 5,482,958 | 1/1996 | Bryant et al. | 514/408 |
| 5,563,133 | 10/1996 | Hipskind et al. | 514/212 |

OTHER PUBLICATIONS

Giunchedi et al Journal of Pharmacy and Pharmacology, 46(6), 476–80 (Abstract), 1994.

*Primary Examiner*—Raymond Henley, III
*Attorney, Agent, or Firm*—Steve T. Zelson; Carol E. Rozek

[57] ABSTRACT

The present invention relates to a pharmaceutical formulation for oral administration which comprises a compound of formula I

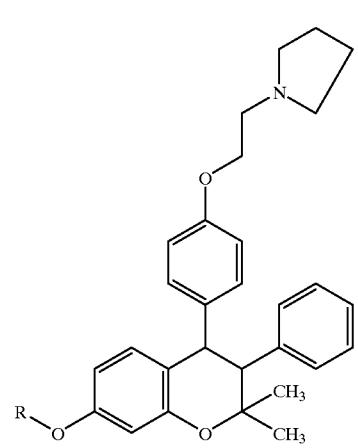

wherein R is $C_{1-6}$alkyl; or a pharmaceutically acceptable salt thereof, in combination with a hydrophilic binder and a water-soluble diluent.

18 Claims, No Drawings

PHARMACEUTICAL FORMULATIONS COMPRISING LEVORMELOXIFENE COMPOUNDS

This application claims priority under 35 U.S.C. 119 to U.S. provisional patent application Serial No. 60/039,351, filed Mar. 18, 1997, and Danish applications 1359/96 filed Nov. 28, 1996 and 1265/97 filed Nov. 7, 1997, the contents of which are fully incorporated herein by reference.

FIELD OF THE INVENTION

This invention relates to new pharmaceutical formulations for oral administration comprising certain 3,4-diarylchromans of formula I, or a pharmaceutically acceptable salt thereof, in combination with a hydrophilic binder and a water-soluble diluent.

The 3,4-diarylchromans of formula I

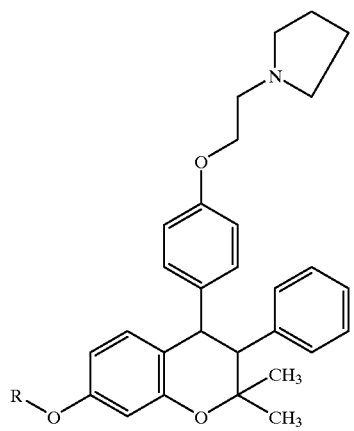

(I)

wherein R is $C_{1-6}$alkyl, and pharmaceutically acceptable salts thereof are known to be useful for reducing bone loss.

BACKGROUND OF THE INVENTION

The formula I compounds are described in U.S. Pat. No. 5,280,040. This patent describes the preparation of these compounds, as well as their use for reducing bone loss. The preparation of pharmaceutical compositions is also described.

Centchroman, which is 3,4-trans-2,2-dimethyl-3-phenyl-4-[4-(2-pyrrolidin-1-yl)ethoxy)phenyl]-7-methoxychroman, is a non-steroidal compound known to have antiestrogenic activity. It is in use in India as an oral contraceptive (see, for example, Salman et al., U.S. Pat. No. 4,447,622; Singh et al., Acta Endocrinal (Copenh) 126 (1992), 444–450; Grubb, Curr Opin Obstet Gynecol 3 (1991), 491–495; Sankaran et al., Contraception 9 (1974), 279–289; Indian Patent Specification No. 129187). Centchroman has also been investigated as an anti-cancer agent for treatment of advanced breast cancer (Misra et al., Int J Cancer 43 (1989), 781–783. Recently, centchroman as a racemate has been found as a potent cholesterol lowering pharmaceutical agent expressed by a significant decrease of the serum concentrations (S. D. Bain et al., J Min Bon Res 9 (1994), S 394).

Levormeloxifene, (−)-3R,4R-trans-7-methoxy-2,2-dimethyl-3-phenyl-4-{4-[2-(pyrrolidin-1-yl)ethoxy]phenyl}chromane, is a particular preferred compound from this series of 3,4-diarylchromans. Levormeloxifene may be used in human and veterinary medicine for the regulation of bone metabolism. It may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

The 3,4-diarylchromans are prepared according to known methods, such as those disclosed in U.S. Pat. No. 3,340,276 to Carney et. al., U.S. Pat. No. 3,822,287 to Bolger, and Ray et al., J Med Chem 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. The resolution of (±)-3,4-trans-7-methoxy-2,2-dimethyl-3-phenyl-4-{4-[2-(pyrrolidin-1-yl)ethoxy]phenyl}chromane in its optical antipodes is described in U.S. Pat. No. 4,447,622 incorporated herein by reference. Example 1 of U.S. Pat. No. 4,447,622 describes the preparation of the minus enantiomer, shown by formula II:

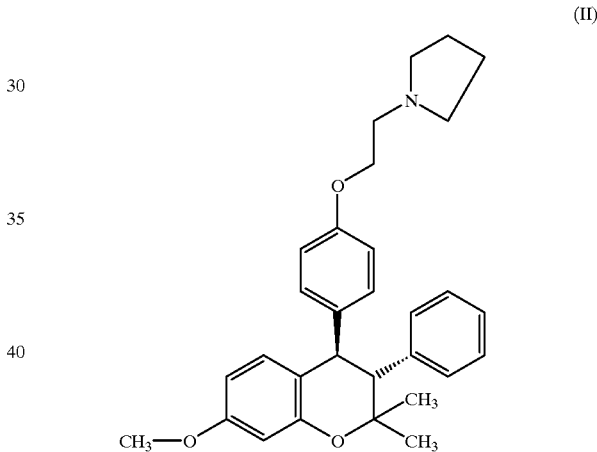

(II)

(In this specification, the compound of formula II is referred to as levormeloxifene.) In example 2 of U.S. Pat. No. 4,447,622, levormeloxifene is obtained as the free base and the hydrochloride salt.

The compounds of formula I may be administered as pharmaceutically acceptable salts. A particularly useful pharmaceutically acceptable salt of levormeloxifene is the hydrogen fumarate salt (in this specification, this compound is referred to as levormeloxifene fumarate.). This salt form is prepared by dissolving fumaric acid and (−)-3R,4R-trans-7-methoxy-2,2-dimethyl-3-phenyl-4-{4-[2-(pyrrolidin-1-yl)ethoxy]phenyl}chromane in a common solvent such as e.g. methanol, and crystallizing the resulting salt from the solution.

An object of the present invention is to provide a pharmaceutical formulation for oral administration which formulation has a favourable bioavailability.

The present invention provides a pharmaceutical formulation for oral administration comprising a compound of formula I, or a pharmaceutically acceptable salt thereof, in combination with a hydrophilic carrier composition. Such formulations have an increased solubility in aqueous media.

The present invention provides a pharmaceutical formulation for oral administration which comprises a compound of formula I

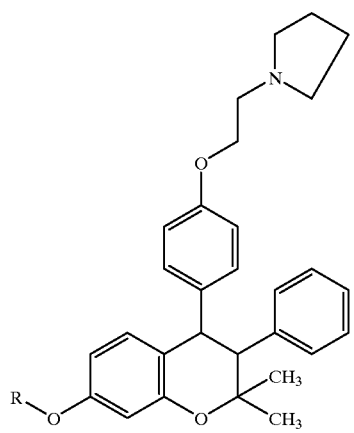

(I)

wherein R is $C_{1-6}$alkyl; or a pharmaceutically acceptable salt thereof, a hydrophilic binder and a water-soluble diluent. According to a preferred embodiment of the invention, the formulation further comprises a surfactant. The present invention also provides pharmaceutical formulations further comprising a lubricant and/or disintegrant. To further improve the stability of the formulation according to the invention, a suitable antioxidant or a combination of antioxidants may be used. It is preferred to use the compounds of formula I in the trans configuration. The l enantiomeric forms are preferred over racemic mixtures. Within particularly preferred embodiments, R is methyl.

The general chemical terms used in the above formula have their usual meanings.

As used herein, the term "$C_{1-6}$alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like.

The term "pharmaceutically acceptable salt" represents salt forms of a compound of formula I that are physiologically suitable for pharmaceutical use. The pharmaceutically acceptable salts can exist in conjunction with a compound of formula I as acid addition primary, secondary, tertiary, or quaternary ammonium, alkali metal, or alkaline earth metal salts. Generally, the acid addition salts are prepared by the reaction of an acid with a compound of formula I, wherein R is as defined previously. The alkali metal and alkaline earth metal salts are generally prepared by the reaction of the metal hydroxide of the desired metal salt with a compound of formula I, wherein R is hydrogen.

Within the present invention, the compounds of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The term "hydrophilic binder" represents binders commonly used in the formulation of pharmaceuticals, such as polyvinylpyrrolidone, copolyvidone (cross-linked polyvinylpyrrolidone), polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "water-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "non water-soluble diluent" represents compounds typically used in the formulation of pharmaceuticals, such as calcium phosphate, calcium sulfate, starches, modified starches and microcrystalline cellulose.

The term "non water-soluble diluent with non-swelling properties" represents the non water-soluble diluents as indicated above, but excluding starches and modified starches and the like.

The term "surfactant", as used herein, represents ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, alcohols and phospholipids.

The term "antioxidant" represents the three groups of antioxidants, true antioxidants, reducing agents and antoxidant synergists, such as tocopherols, tocopherolesters, alkyl gallates, butylated hydroxyanisole, butylated hydroxytoluene, ascorbic acid, citric acid, edetic acid and its salts, lecithin and tartaric acid.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably, the disintegrant is a modified cellulose gum such as e.g. cross-linked sodium carboxymethylcellulose.

The term "lubricant" represents compounds frequently used as lubricants or glidants in the preparation of pharmaceuticals, such as talc, magnesium stearate, calcium stearate, stearic acid, colloidal silicon dioxide, magnesium carbonate, magnesium oxide, calcium silicate, microcrystalline cellulose, starches, mineral oil, waxes, glyceryl behenate, polyethylene glycol, sodium benzoate, sodium acetate, sodium chloride, sodium laurylsulfate, sodium stearyl fumarate, and hydrogenated vegetable oils. Preferably, the lubricant is magnesium stearate or talc, more preferably magnesium stearate and talc in combination.

All formulations of the present invention have an increased solubility in aqueous media and therefore, greater bioavailability would be expected. In a bioavailability study in humans comparing a solution of levormeloxifene and a levormeloxifene tablet formulation a bioequivalency of 100% was obtained.

In one preferred embodiment of the invention, the hydrophilic binder is gelatin, cellulose derivative, polyvinylpyrrolidone or copolyvidone.

In another preferred embodiment of the invention, the water-soluble diluent is a sugar, a polysaccharide or cyclodextrin.

In another preferred embodiment of the invention, the formulation further comprises a non water-soluble diluent. In one embodiment thereof the non water-soluble diluent is a non water-soluble diluent with non-swelling properties, preferably microcrystalline cellulose.

In another preferred embodiment of the invention, the formulation further comprises an antioxidant. Preferably the antioxidant is tocopherols and tocopherolesters, such as alpha-tocopherol succinate.

In another preferred embodiment of the invention, the formulation further comprises a surfactant. When the surfactant is present, preferably it is an anionic or nonionic surfactant. Representative surfactants from this preferred group include sodium laurylsulfate, polyglycolyzed glycerides, polyoxyethylene sorbitan fatty acid esters, monoglycerides, diglycerides or glycerol.

In another preferred embodiment of the invention, the formulation further comprises a lubricant(s) and/or a disintegrant.

Certain formulations of the present invention are more preferred. More preferably, the hydrophilic binder is polyvinylpyrrolidone or copolyvidone. More preferably, the water-soluble diluent is a sugar, such as lactose, sucrose, dextrose. More preferably, the surfactant is a nonionic surfactant, such as polyoxyethylene sorbitan fatty acid esters or glycerol.

Certain formulations of the present invention are most preferred. Most preferably, the hydrophilic binder is copolyvidone. Most preferably, the water-soluble diluent is lactose. Most preferably, the surfactant, when present, is glycerol.

The amount of hydrophilic binder in the pharmaceutical formulation according to the invention is preferably from about 1% to about 25% (w/w), more preferably from about 1% to about 15% (w/w), most preferably from about 2.5% to about 15% (w/w).

The amount of water-soluble diluent in the pharmacutical formulation according to the invention is preferably from about 20% to about 98% (w/w), more preferred from about 20% to about 80% (w/w).

The amount of non water-soluble diluent in the pharmacutical formulation according to the invention is preferably from about 1% to about 50% (w/w), more preferred from about 5% to about 30% (w/w).

The amount of the compound of formula I in the pharmaceutical formulation according to the invention is preferably from about 0.05% to about 50% (w/w), such as from about 0.1% to about 40% (w/w).

The orally administerable formulations of the present invention are prepared and administered according to methods well known in pharmaceutical chemistry, see Remington's Pharmaceutical Sciences, 17$^{th}$ ed. (A. Osol ed., 1985). For example, the compositions of the present invention may be administered by means of solid dosage forms such as tablets and capsules. Preferably, the compositions are formulated as tablets. These tablets may be prepared by wet granulation, by dry granulation, or by direct compression.

Tablets for this invention are prepared utilizing conventional tabletting techniques. A general method of manufacture involves blending of a compound of formula I, or a salt thereof, the water-soluble diluent, hydrophilic binder and optionally a portion of a disintegrant. This blend is then granulated with an aqueous solution of the hydrophilic binder or an aqueous solution of the hydrophilic binder and surfactant and milled, if necessary. The granules are dried and reduced to a suitable size. Any other ingredients, such as lubricants, (e.g. magnesium stearate) and additional disintegrants, are added to the granules and mixed. This mixture is then compressed into a suitable size and shape using conventional tabletting machines such as a rotary tablet press. The tablets may be film coated by techniques well known in the art.

Capsules for this invention are prepared utilizing conventional methods. A general method of manufacture involves blending of a compound of formula I, or a salt thereof, the water-soluble diluent, a hydrophilic binder, and optionally a portion of a disintegrant. This blend is then granulated with an aqueous solution of the hydrophilic binder or an aqueous solution of the hydrophilic binder and surfactant in water, and milled, if necessary.

The granules are dried and reduced to a suitable size. Any other ingredients, such as a lubricant, are added to the granules and mixed. The resulting mixture is then filled into a suitable size hard-shell gelatin capsule using conventional capsule-filling machines.

The following formulation examples are illustrative only and are not intended to limit the scope of the invention in any way.

The preferred range of pharmaceutical formulation (such as solid dosage form, e.g. capsule or tablet) strength may be from about 0.125 mg to about 40 mg of a compound of formula I, more preferred from about 0.25 mg to about 5 mg of a compound of formula I, preferably levormeloxifene.

The preferred range of total mass may be from about 40 mg to about 500 mg depending on the strength of the formulation, more preferred from about 80 mg to about 320 mg.

Tablets and capsules may be prepared using the ingredients and procedures as described below:

FORMULATION 1

| Ingredient | weight (mg/tablet) |
| --- | --- |
| Levormeloxifene fumarate corresponding to 10 mg base | 12.54 mg |
| Microcrystalline cellulose | 48.00 mg |
| Cross-carmellose sodium | 25.00 mg |
| Copolyvidone | 24.00 mg |
| Lactose | 206.00 mg |
| Magnesium stearate | 1.00 mg |
| Talc | 3.20 mg |

The mixture of levormeloxifene fumarate, lactose, microcrystalline cellulose, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 320 mg. It is possible to manufacture levormeloxifene tablet strengths in the range of 1.25 mg to 40 mg with a total mass of 320 mg.

FORMULATION 2

| Ingredient | weight (mg/tablet) |
| --- | --- |
| Levormeloxifene fumarate corresponding to 5 mg base | 6.27 mg |
| Microcrystalline cellulose | 24.00 mg |

-continued

| Ingredient | weight (mg/tablet) |
| --- | --- |
| Cross-carmellose sodium | 12.50 mg |
| Copolyvidone | 12.00 mg |
| Lactose | 102.85 mg |
| Magnesium stearate | 0.80 mg |
| Talc | 1.60 mg |

The mixture of levormeloxifene fumarate, lactose, microcrystalline cellulose, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 160 mg. It is possible to manufacture levormeloxifene tablet strengths in the range of 0.25 mg to 40 mg with a total mass of 160 mg.

FORMULATION 3

| Ingredient | weight (mg/tablet) |
| --- | --- |
| Levormeloxifene fumarate corresponding to 5 mg base | 6.27 mg |
| Microcrystalline cellulose | 18.00 mg |
| Cross-carmellose sodium | 9.36 mg |
| Copolyvidone | 9.00 mg |
| Lactose | 75.57 mg |
| Magnesium stearate | 0.60 mg |
| Talc | 1.20 mg |

The mixture of levormeloxifene fumarate, lactose, microcrystalline cellulose, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 320 mg. It is possible to manufacture levormeloxifene tablet strengths in the range of 0.125 mg to 20 mg with a total mass of 120 mg.

FORMULATION 4

| Ingredient | weight (mg/tablet) |
| --- | --- |
| Levormeloxifene fumarate corresponding to 40 mg base | 50.00 mg |
| Microcrystalline cellulose | 48.00 mg |
| Cross-carmellose sodium | 25.00 mg |
| Copolyvidone | 24.00 mg |
| Na-laurylsulfate | 6.40 mg |
| Lactose | 161.80 mg |
| Magnesium stearate | 1.60 mg |
| Talc | 3.20 mg |

The mixture of levormeloxifene fumarate, lactose, microcrystalline cellulose, and a portion of cross-carmellose sodium and copolyvidone is granulated with an aqueous solution of copolyvidone containing dissolved sodium laurylsulfate. The granules are dried, reduced to a suitable size and mixed with magnesium stearate, talc and remaining cross-carmellose sodium. The mixture is compressed into individual tablets yielding a tablet weight of 320 mg. It is possible to manufacture levormeloxifene tablet strengths in the range of 1.25 mg to 40 mg with a total mass of 320 mg.

FORMULATION 5

| Ingredient | weight (mg/tablet) |
| --- | --- |
| Levormeloxifene fumarate corresponding to 40 mg base | 50.00 mg |
| Dextrose | 168.20 mg |
| Microcrystalline cellulose | 48.00 mg |
| Cross-carmellose sodium | 25.00 mg |
| Copolyvidone | 24.00 mg |
| Magnesium stearate | 1.60 mg |
| Talc | 3.20 mg |

The mixture of levormeloxifene fumarate, dextrose, microcrystalline cellulose, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 320 mg. It is possible to manufacture levormeloxifene tablet strengths in the range of 1.25 mg to 40 mg with a total mass of 320 mg.

FORMULATION 6

| Ingredient | weight (mg/tablet) |
| --- | --- |
| Levormeloxifene fumarate corresponding to 40 mg base | 50.00 mg |
| Microcrystalline cellulose | 70.00 mg |
| Cross-carmellose sodium | 31.25 mg |
| Gelatine | 5.00 mg |
| Lactose | 237.75 mg |
| Magnesium stearate | 2.00 mg |
| Talc | 4.00 mg |

The mixture of levormeloxifene fumarate, lactose, microcrystalline cellulose, and a portion of cross-carmellose sodium is granulated with an aqueous solution of gelatine. The granules are dried, reduced to a suitable size and mixed with magnesium stearate, talc and remaining cross-carmellose sodium. The mixture is compressed into individual tablets yielding a tablet weight of 400 mg. It is possible to manufacture levormeloxifene tablet strengths in the range of 1.25 mg to 40 mg with a total mass of 400 mg.

FORMULATION 7

| Ingredient | weight (mg/tablet) |
| --- | --- |
| Levormeloxifene fumarate corresponding to 40 mg base | 50.00 mg |
| Microcrystalline cellulose | 70.00 mg |
| Cross-carmellose sodium | 31.25 mg |
| Dextrose | 237.75 mg |
| Gelatine | 5.00 mg |
| Magnesium stearate | 2.00 mg |
| Talc | 4.00 mg |

The mixture of levormeloxifene fumarate, dextrose, microcrystalline cellulose, and a portion of cross-carmellose sodium is granulated with an aqueous solution of gelatine. The granules are dried, reduced to a suitable size and mixed with magnesium stearate, talc and remaining cross-carmellose sodium. The mixture is compressed into individual tablets yielding a tablet weight of 400 mg. It is possible to manufacture levormeloxifene tablet strengths in the range of 1.25 mg to 40 mg with a total mass of 400 mg.

FORMULATION 8

| Ingredient | weight (mg/tablet) |
| --- | --- |
| Levormeloxifene fumarate corresponding to 40 mg base | 50.00 mg |
| Microcrystalline cellulose | 60.00 mg |
| Cross-carmellose sodium | 31.25 mg |
| Copolyvidone | 25.00 mg |
| Tween 80 | 3.25 mg |
| Lactose | 224.50 mg |
| Magnesium stearate | 2.00 mg |
| Talc | 4.00 mg |

The mixture of levormeloxifene fumarate, lactose, microcrystalline cellulose, and a portion of cross-carmellose sodium and copolyvidone is granulated with an aqueous solution of copolyvidone containing Tween 80. The granules are dried, reduced to a suitable size and mixed with magnesium stearate, talc and remaining cross-carmellose sodium. The mixture is compressed into individual tablets yielding a tablet weight of 400 mg. It is possible to manufacture levormeloxifene tablet strengths in the range of 1.25 mg to 40 mg with a total mass of 400 mg.

FORMULATION 9

| Ingredient | weight (mg/tablet) |
| --- | --- |
| Levormeloxifene fumarate corresponding to 40 mg base | 50.00 mg |
| Microcrystalline cellulose | 60.00 mg |
| Cross-carmellose sodium | 31.25 mg |
| Copolyvidone | 29.00 mg |
| Glycerol | 3.25 mg |
| Lactose | 220.50 mg |
| Magnesium stearate | 2.00 mg |
| Talc | 4.00 mg |

The mixture of levormeloxifene fumarate, lactose, microcrystalline cellulose, and a portion of cross-carmellose sodium and copolyvidone is granulated with an aqueous solution of copolyvidone containing glycerol. The granules are dried, reduced to a suitable size and mixed with magnesium stearate, talc and remaining cross-carmellose sodium. The mixture is compressed into individual tablets yielding a tablet weight of 400 mg. It is possible to manufacture levormeloxifene tablet strengths in the range of 1.25 mg to 40 mg with a total mass of 400 mg.

FORMULATION 10

| Ingredient | weight (mg/tablet) |
| --- | --- |
| Levormeloxifene fumarate corresponding to 40 mg base | 50.00 mg |
| Microcrystalline cellulose | 68.00 mg |
| Cross-carmellose sodium | 26.25 mg |
| Gelatine | 5.00 mg |
| Glycerol | 6.25 mg |
| Dextrose | 338.50 mg |
| Magnesium stearate | 2.00 mg |
| Talc | 4.00 mg |

The mixture of levormeloxifene fumarate, dextrose, microcrystalline cellulose, and a portion of cross-carmellose sodium is granulated with an aqueous solution of gelatine and glycerol. The granules are dried, reduced to a suitable size and mixed with magnesium stearate, talc and remaining cross-carmellose sodium. The mixture is compressed into individual tablets yielding a tablet weight of 400 mg. It is possible to manufacture levormeloxifene tablet strengths in the range of 1.25 mg to 40 mg with a total mass of 400 mg.

FORMULATION 11

| Ingredient | weight (mg/tablet) |
| --- | --- |
| Levormeloxifene fumarate corresponding to 40 mg base | 50.00 mg |
| Microcrystalline cellulose | 35.00 mg |
| Cross-carmellose sodium | 26.25 mg |
| hydroxypropyl-betacyclodextrin (HP-cd) | 115.00 mg |
| Gelatine | 5.00 mg |
| Glycerol | 6.25 mg |
| Dextrose | 256.50 mg |
| Magnseium stearate | 2.00 mg |
| Talc | 4.00 |

The mixture of levormeloxifene fumarate, dextrose, hydroxypropyl-betacyclodextrin microcrystalline cellulose, and a portion of cross-carmellose sodium is granulated with an aqueous solution of gelatine containing glycerol. The granules are dried, reduced to a suitable size and mixed with magnesium stearate, talc and remaining cross-carmellose sodium. The mixture is compressed into individual tablets yielding a tablet weight of 500 mg. It is possible to manufacture levormeloxifene tablet 10 strengths in the range of 1.25 mg to 80 mg with a total mass of 500 mg.

FORMULATION 12 AND 13

| Ingredient | Weight |
| --- | --- |
| Levormeloxifene fumarate corresponding to 5 mg base | 6.27 mg |
| Lactose | 395.1 mg |
| Microcrystalline cellulose | 9.875 mg |
| Polyvinylpyrrolidone/copolyvidone | 8.400 mg |
| Magnesium stearate | 0.375 mg |

The mixture of levormeloxifene fumarate, lactose and microcrystalline cellulose is granulated with an aqueous solution of polyvinylpyrrolidone or copolyvidone. The granules are dried, reduced to a suitable size and mixed with magnesium stearate. The mixture is then filled into size 0 hard-shell gelatine capsules utilizing conventional encapsulating equipment. In order to obtain different capsule strenghts in the range of 1.25 mg to 20.0 mg, different quantities are weighed out in the range of 15 mg to 240 mg.

FORMULATION 14

| Ingredient | Weight (mg/tablet) |
| --- | --- |
| Levormeloxifene fumarate corresponding to 0.25 mg base | 0.313 mg |
| Microcrystalline Cellulose | 12.00 mg |
| Cross-Carmellose Sodium | 6.25 mg |
| Copolyvidone | 6.00 mg |
| Lactose | 54.20 mg |
| Alpha-tocopherol Succinate | 0.0308 mg |
| Magnesium Stearate | 0.40 mg |
| Talc | 0.80 mg |

The mixture of levormeloxifene fumarate, lactose, microcrystalline cellulose, antioxidant, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 80 mg. It is possible to manufacture levormeloxifene tablet strengths in the range of 0.125 mg to 10 mg with a total mass of 80 mg.

FORMULATION 15

| Ingredient | Weight (mg/tablet) |
| --- | --- |
| Levormeloxifene fumarate corresponding to to 0.25 mg base | 3.13 mg |
| Microcrystalline Cellulose | 15.00 mg |
| Cross-Carmellose Sodium | 7.75 mg |
| Copolyvidone | 7.50 mg |
| Lactose | 64.80 mg |
| Alpha-tocopherol Succinate | 0.0308 mg |
| Magnesium Stearate | 0.50 mg |
| Talc | 1.00 mg |

The mixture of levormeloxifene fumarate, lactose, microcrystalline cellulose, antioxidant, and a portion of cross-carmellose sodium and copolyvidone is granulated with an aqueous solution of copolyvidone. The granules are dried, reduced to a suitable size and mixed with magnesium stearate, talc and remaining cross-carmellose sodium. The mixture is compressed into individual tablets yielding a tablet weight of 100 mg. It is possible to manufacture levormeloxifene tablet strengths in the range of 0.125 mg to 20 mg with a total mass of 100 mg.

What is claimed is:

1. A pharmaceutical formulation for oral administration as a solid dosage form which formulation comprises a compound of formula I

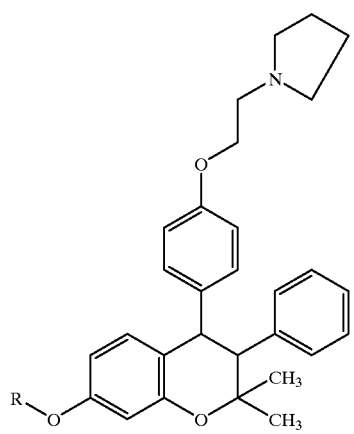

(I)

wherein R is $C_{1-6}$alkyl; or a pharmaceutically acceptable salt thereof, in combination with a hydrophilic binder and a water-soluble diluent, wherein the compound of formula I is present in an amount from about 0.05% to about 50% (w/w), the hydrophilic binder in an amount from about 1% to about 25% (w/w) and the water-soluble diluent in an amount from about 20% to about 98% (w/w), all percentages being based on the total weight of the formulation, wherein the solid dosage form has increased solubility in aqueous media and is bioequivalent to a solution containing a compound of formula I, as measured in a bioavailability study in humans comparing a solution of levormeloxifene with a tablet formulation of levormeloxifene.

2. The formulation according to claim 1 wherein said hydrophilic binder is cross-linked polyvinylpyrrolidone.

3. The formulation according to claim 1 wherein said water-soluble diluent is lactose.

4. The formulation according to claim 1 further comprising a surfactant.

5. The formulation according to claim 4 wherein said surfactant is glycerol.

6. The formulation according to claim 1 comprising a compound of formula I, and further comprising lactose, copolyvidone, talc, magnesium stearate, microcrystalline cellulose and cross-carmellose sodium.

7. The formulation according to claim 1 further comprising an antioxidant.

8. The formulation according to claim 7 wherein said antioxidant is alpha-tocopherol succinate.

9. The formulation according to claim 1 further comprising a non water-soluble diluent.

10. The formulation according to claim 9 wherein said non water-soluble diluent is microcrystalline cellulose.

11. The formulation according to claim 1 wherein said dosage form is a tablet.

12. The formulation according to claim 1 further comprising a film coating.

13. The formulation according to claim 1 wherein R in the compound of formula I is methyl.

14. The formulation according to claim 1 wherein said compound of formula I is in the trans configuration.

15. The formulation according to claim 1 wherein said compound of formula I is 3,4-trans-2,2-dimethyl-3-phenyl-4-[4-(2-pyrrolidin-1-yl)ethoxy)phenyl]-7-methoxychroman or a salt thereof.

16. The formulation according to claim 1 wherein said compound of formula I is an isolated l-enantiomer or a salt thereof.

17. The formulation according to claim 1 wherein said compound of formula I is (−)-3R,4R-trans-7-methoxy-2,2-dimethyl-3-phenyl-4-{4-[2-(pyrrolidin-1-yl)ethoxy]phenyl}chromane or a salt thereof.

18. The formulation according to claim 17 wherein said compound of formula I is in the form of the hydrogen fumarate salt.

* * * * *